Figure 1:
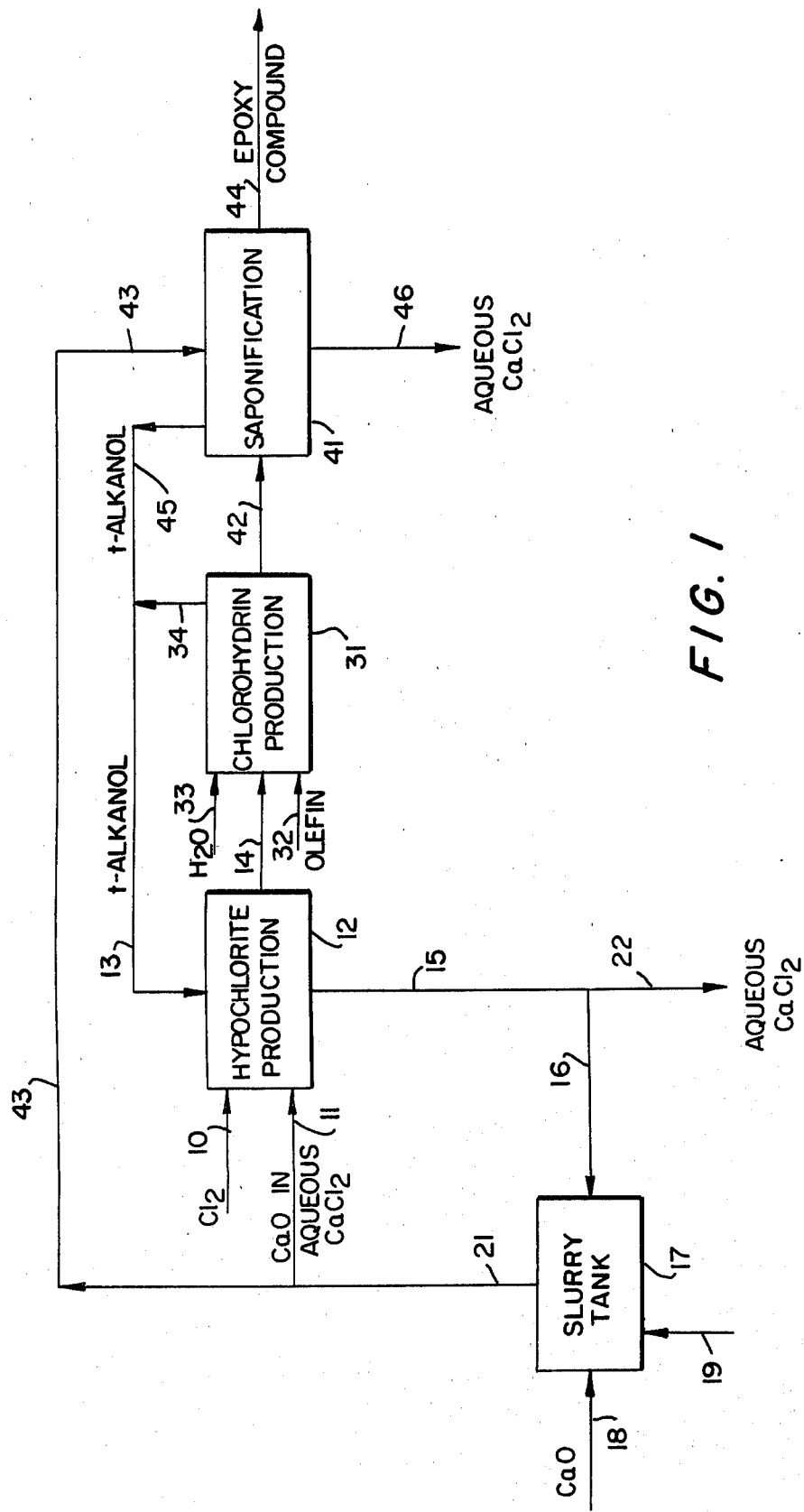

United States Patent [19]

Apanel

[11] 4,410,714

[45] Oct. 18, 1983

[54] PRODUCTION OF EPOXY COMPOUNDS FROM OLEFINIC COMPOUNDS

[75] Inventor: George J. Apanel, Bloomfield, N.J.

[73] Assignee: The Lummus Company, Bloomfield, N.J.

[21] Appl. No.: 35,559

[22] Filed: May 3, 1979

[51] Int. Cl.$^3$ .......................................... C07D 301/26
[52] U.S. Cl. .................................... 549/521; 549/520; 549/522
[58] Field of Search ...................... 260/348.21, 348.22, 260/348.18, 453 R; 549/520, 521, 522

[56] References Cited

U.S. PATENT DOCUMENTS

| | | | |
|---|---|---|---|
| 1,938,175 | 12/1933 | Deanesly | 260/453 R X |
| 2,694,722 | 11/1954 | Katz | 260/453 R X |
| 4,008,133 | 2/1977 | Gelbein et al. | 260/348.18 |
| 4,126,526 | 11/1978 | Kwon et al. | 260/348.21 |

FOREIGN PATENT DOCUMENTS 1291328  3/1969  Fed. Rep. of Germany ...................... 260/348.21

Primary Examiner—Norma S. Milestone
Attorney, Agent, or Firm—Elliot M. Olstein; Louis E. Marn

[57] ABSTRACT

A process for producing an epoxy compound by chlorinating a tertiary alkanol to the corresponding hypochlorite, followed by reaction of the hypochlorite with water and an olefinically unsaturated compound to produce the corresponding chlorohydrin and saponification of the chlorohydrin to the corresponding epoxy compound. The hypochlorite production and the saponification are effected with calcium oxide in an aqueous solution of calcium chloride, with calcium chloride being produced as by-product in an aqueous solution having a calcium chloride concentration of at least 25 wt. %. In this manner, calcium chloride by-product is recovered in a more usable form thereby eliminating the problems associated with recovery of calcium chloride by-product.

7 Claims, 2 Drawing Figures

PRODUCTION OF EPOXY COMPOUNDS FROM OLEFINIC COMPOUNDS

This invention relates to the production of epoxy compounds, and more particularly, to a new and improved process for producing epoxy compounds from olefinically unsaturated compounds via the chlorohydrin.

In the production of an epoxy compound, such as propylene oxide, by conversion of propylene to the chlorohydrin, it is known to saponify and neutralize such chlorohydrin by the use of calcium hydroxide. In accordance with such known processes, however, difficulties have been encountered in recovering and disposing of calcium chloride produced as by-product in such process.

In U.S. Pat. No. 4,008,133, there is disclosed a process for producing an epoxy compund from olefinically unsaturated compound, which is integrated with an electrolytic cell for producing chlorine. In accordance with such process, a tertiary alkanol is converted to the corresponding hypochlorite in the presence of caustic cell liquor, with the hypochlorite being subsequently reacted with water and olefin to produce the chlorohydrin, which is then saponified and neutralized with caustic cell liquor. The brine solution produced in the hypochlorite production and saponification is recycled, as electrolyte to the cell. In this manner, the epoxy compound is produced from water and olefin, as net starting materials.

In many cases, however, there may be a high market value for the caustic produced in the cell, whereby it may be more economical to sell such caustic instead of using such for the production of the epoxy compound.

The present invention is directed to a new and improved process for producing an epoxy compound from an olefin, via the chlorohydrin, without the difficulties previously encountered in recovering by-products generated in the process.

In accordance with the present invention, there is provided an improvement in a process for producing an epoxy compound wherein a tertiary alkanol is chlorinated to the tertiary alkyl hypochlorite, followed by reacting the hypochlorite with water and olefinically unsaturated compound to produce the corresponding chlorohydrin, which is saponified to the epoxy compound, with such improvement resulting from conducting the chlorination of the tertiary alkanol and the saponification of the chlorohydrin with calcium oxide in an aqueous solution of calcium chloride, with the aqueous calcium chloride solution which is recovered from the hypochlorite production and saponification having a calcium chloride concentration of at least 25%, by weight.

The concentration of the calcium chloride recovered as by-product is determined by the concentration of the combined calcium oxide and calcium chloride employed in the hypochlorite production and saponification. The specific amount of calcium chloride employed is determined in part by the desired concentration of calcium chloride in the by-product and in part by the solubility of calcium oxide in aqueous calcium chloride. Thus, higher calcium chloride by-product concentrations are favored by higher concentrations of calcium chloride in the solution employed for hypochlorite production and saponification (for example, saturated as to calcium chloride); however, calcium oxide solubility requirements may dictate lower concentrations of calcium chloride; e.g., maximum calcium oxide solubility may occur in a solution having a combined calcium oxide and calcium chloride concentration, equivalent of from 30% to 45%, as calcium chloride. Thus, in general, the combined calcium oxide and calcium chloride has a concentration equivalent to at least 25%, generally at least 30%, all by weight expressed as calcium chloride. The maximum concentration is a saturated solution (about 65 weight percent). In some cases, in order to maximize calcium oxide solubility, the combined concentration may be in the order of 30% to 45%, by weight, expressed as calcium chloride. It is to be understood that such concentrations for the hypochlorite production and saponification may be identical to or different than each other. It is also to be understood that in some cases the calcium oxide may be present in excess of its solubility; e.g., as a partial slurry. The calcium chloride concentration in the by-product produced in the process (prior to treatment, if any, to further concentrate the calcium chloride) corresponds to the hereinabove noted equivalent calcium chloride concentrations. Thus in accordance with the present invention, it is possible in some cases to recover calcium chloride as a saturated aqueous solution at the processing conditions. Thus, by providing the base requirements for the process as calcium oxide in an aqueous calcium chloride solution, the calcium chloride by-product is recovered in a more concentrated and usable form, thereby eliminating the problems heretofore encountered in the art in attempting to recover calcium chloride by-product resulting from the use of calcium oxide in the production of an epoxy compound.

More particularly, chlorine is reacted with a tertiary alkanol, preferably a tertiary alkanol having from 4 to 6 carbon atoms, and most preferably tertiary butanol or tertiary amylalcohol, and calcium oxide in an aqueous calcium chloride solution. Calcium chloride and calcium oxide are present in amounts as hereinabove described.

In general, the hypochlorite production is effected at a temperature in the order of from about 5° to about 220° F., preferably at a temperature from about 32° to about 160° F., with the pressure generally being from about 5 psia to 100 psia, preferably from about 10 psia to 50 psia.

In effecting the production of hypochlorite, in order to minimize the amount of free chlorine present in the alkyl hypochlorite introduced as feed to the chlorohydrin production reactor, the hypochlorite production reaction should be effected without a substantial molar excess of chlorine with respect to calcium oxide.

In accordance with the present invention, as a result of providing the calcium oxide to the hypochlorite production in an aqueous calcium choride solution, the calcium choride solution recovered from the hypochlorite production has a calcium chloride concentration as hereinabove described, which corresponds to the equivalent calcium chloride in the feed. Such aqueous calcium chloride solution may be used as such, or may be further concentrated; for example in an evaporator, and then flaked or spray-dried to produce a powdered product.

The hypochlorite is then employed for the production of a chlorohydrin by reaction with water and olefinically unsaturated compound. Such chlorohydrin production may be accomplished as described in U.S. Pat. No. 4,008,133, which is hereby incorporated by reference. As noted in such patent, the chlorohydrin is preferably contacted with water which is essentially free of chloride ion; i.e., the water should not contain a chloride ion concentration in excess of 1 mole per liter and preferably the chloride ion concentration should not exceed 0.3 mole per liter. Furthermore, as disclosed in the patent, the amount of free chlorine is maintained as low as possible in order to minimize by-product production. Such chlorohydrin production is generally accomplished at a temperature from about B 32° to about 160° F., and preferably at a temperature from about 70° to about 140° F., with the pressure generally being in the order of about 1 psig to 300 psig, preferably atmospheric pressure.

The chlorohydrin production reaction effluent contains water, chlorohydrin, tertiary alkanol, as well as by-products.

The chlorohydrin production effluent is then generally treated to separate the aqueous portion therefrom, with such aqueous portion being recycled to the chlorohydrin production reactor. Such separation may be accomplished as described in U.S. Pat. No. 4,008,133. In addition, if desired, as disclosed in U.S. Pat. No. 4,008,133, tertiary alkanol may also be separated from the chlorohydrin effluent at such time.

Alternatively, and preferably, as described in copending U.S. application Ser. No. 35,560 filed on May 3, 1979 an organic extraction solvent may be employed to extract organics from the chlorohydrin production effluent, with chlorohydrin, as well as tertiary alkanol being extracted into the organic phase, with the aqueous phase being recycled to the chlorohydrin production reactor. The organic extraction solvent could be added to the effluent, or in the alternative could be introduced into the chlorohydrin production reactor. In general, such extraction is effected at an elevated temperature in that higher temperatures tend to favor the equilibrium concentration of the tertiary alkanol in the organic extraction solvent. This is particularly true where the aqueous concentration in the effluent is low; i.e., ten weight percent or lower. Thus, for example, such extraction may be effected at temperatures in the order of from about 150° to 200° F. in order to favor the equilibrium concentration of the tertiary alkanol into the organic solvent phase. As hereinafter indicated, the presence of salt in the aqueous phase also favors extraction of organics.

In accordance with a preferred procedure, it has been found that the presence of some salt in the aqueous portion of the chlorohydrin effluent favors extraction of the chlorohydrin and t-alkanol product into the organic phase, thereby facilitating subsequent separation of the effluent into an aqueous phase, for recycle to the chlorohydrin production, and an organic phase, which includes the t-alkanol and chlorohydrin as feed to the saponification. Such salts may include one or more of sodium chloride, sodium sulfate, sodium carbonate, potassium carbonate, calcium chloride, potassium fluoride, etc. Sodium sulfate may be preferred. The salt is employed in concentration which enhances extraction of organics into the organic phase without adversely affecting chlorohydrin production. Thus, if the salt is a chloride, the chloride ion concentration should be below 1 mole per liter of water.

In any event, chlorohydrin, which may further contain tertiary alkanol and organic solvent, is saponified to the corresponding epoxy compound. In accordance with the present invention, the saponification is conducted by the use of calcium oxide in an aqueous calcium chloride solution. The aqueous calcium chloride solution has an equivalent calcium chloride concentration as hereinabove described. In general, such saponification is effected at a temperature from about 150° to 250° F., preferably, from about 180° to about 230° F., at the autogenous pressure of the system. As a result of such saponification, the chlorohydrin is converted to the epoxy compound, and the hydrogen chloride is neutralized to produce calcium chloride and water. The saponification is preferably effected in combination with a stripping operation to recover the epoxy compound, in crude form, as product.

In accordance with the embodiment wherein chlorohydrin is essentially the only organic feed to the saponification, after separation of epoxy product, there remains an aqueous solution of calcium chloride, having a calcium chloride concentration which corresponds to the equivalent calcium chloride concentration in the feed. Such calcium chloride solution may be employed, as hereinabove described, with reference to the hypochlorite production.

In the case where an organic solvent is present in the feed to the saponification, there is recovered an organic phase, and an aqueous phase, containing the calcium chloride. In accordance with one procedure, as disclosed in U.S. application Ser. No. 35,560, the aqueous phase further includes the tertiary alkanol, and such aqueous phase is recycled to the hypochlorite production wherein the tertiary alkanol is converted to hypochlorite, as hereinabove described. Thus, calcium chloride by-product generated in the saponification, as well as calcium chloride by-product generated in the hypochlorite production, are recovered simultaneously from the hypochlorite production step.

In the case where tertiary alkanol and organic extraction solvent are present in the feed to the saponification, tertiary alkanol may be recovered for recycled to the hypochlorite production in accordance with the procedure disclosed in U.S. application Ser. No. 35,560 filed on May 3, 1979. In accordance with such a procedure, the tertiary alkanol is recovered from the saponification by extraction into an aqueous calcium chloride phase comprised of at least one of the aqueous calcium chloride produced in the saponification and the aqueous calcium chloride produced in the hypochlorite production. Thus, for example, in accordance with one embodiment, after recovery of the epoxy compound, the saponification effluent is separated into an aqueous calcium chloride phase which contains the tertiary alkanol, and an organic solvent phase. The organic extraction solvent phase is recycled to the chlorohydrin effluent extraction step, and the aqueous calcium chloride phase, containing the tertiary alkanol, is recycled to the hypochlorite production, with aqueous calcium chloride produced in the saponification being ultimately recovered with the aqueous calcium chloride produced in the hypochlorite production. The tertiary alkanol carrying capacity of such a phase may be increased by increasing the volume thereof; e.g., by addition of a portion of the aqueous calcium chloride recovered from the hypochlorite production and/or a portion of the calcium oxide in aqueous calcium chloride which is to be introduced as feed to the hypochlorite production.

In accordance with another embodiment, the tertiary alkanol is recovered from the saponification in the organic extraction solvent, with aqueous calcium chloride being separately recovered. The tertiary alkanol present in the organic extraction solvent is then extracted therefrom by use of a portion of the aqueous calcium chloride recovered from the hypochlorite production, with the tertiary alkanol being recycled to the hypochlorite production in the aqueous calcium chloride.

As described in such application, extraction of the tertiary alkanol into the aqueous phase is favored by lower temperatures; e.g., 90° F. to 115° F. and lower salt concentrations, whereas extraction of the tertiary alkanol into the organic phase is favored by higher aqueous salt concentrations and higher temperatures; e.g., 150° to 200° F. The selection of suitable salt concentrations and temperatures to achieve the desired extraction equilibrium between the aqueous and organic phases is deemed to be within the scope of those skilled in the art from the teachings herein.

In accordance with the embodiments of the invention wherein an organic extraction solvent is employed, such organic extraction solvent may be any one of a wide variety of extraction solvents which are inert, immiscible with the aqueous phases present in the processes and a solvent for the tertiary alkanol and chlorohydrin employed and/or produced in the process. The term "inert" as used herein means that the extraction solvent does not adversely affect the various reactions. As representative examples of suitable extraction solvents, there may be mentioned: chlorinated hydrocarbons, including chlorinated aromatics, and chlorinated aliphatics (saturated); e.g., chlorobenzene, chlorinated paraffins, such as carbon tetrachloride, chloroform, chlorinated ethers; ketones, and the like. Such solvents may be employed alone or as a mixture of two or more thereof.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formla:

$$R_1-CH=CH-R_2$$

wherein $R_1$ and $R_2$ are each separately either hydrogen; alkyl; halo, naphthyl or phenyl substituted alkyl; halo or alkyl substituted phenyl; phenyl; naphthyl; halo or alkyl substituted naphthyl; alkenyl or halo substituted alkenyl; and $R_1$ and $R_2$ can be linked together to provide a cycloalkane (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexene; stilbene; butadiene; chloroprene; allyl chloride, allyl bromide; bromoprene; cyclohexene, and cyclopentene. The epoxy compounds generally produced in accordance with the invention are represented by the following structural formula:

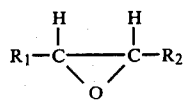

wherein $R_1$ and $R_2$ are as defined above.

Figure 2:
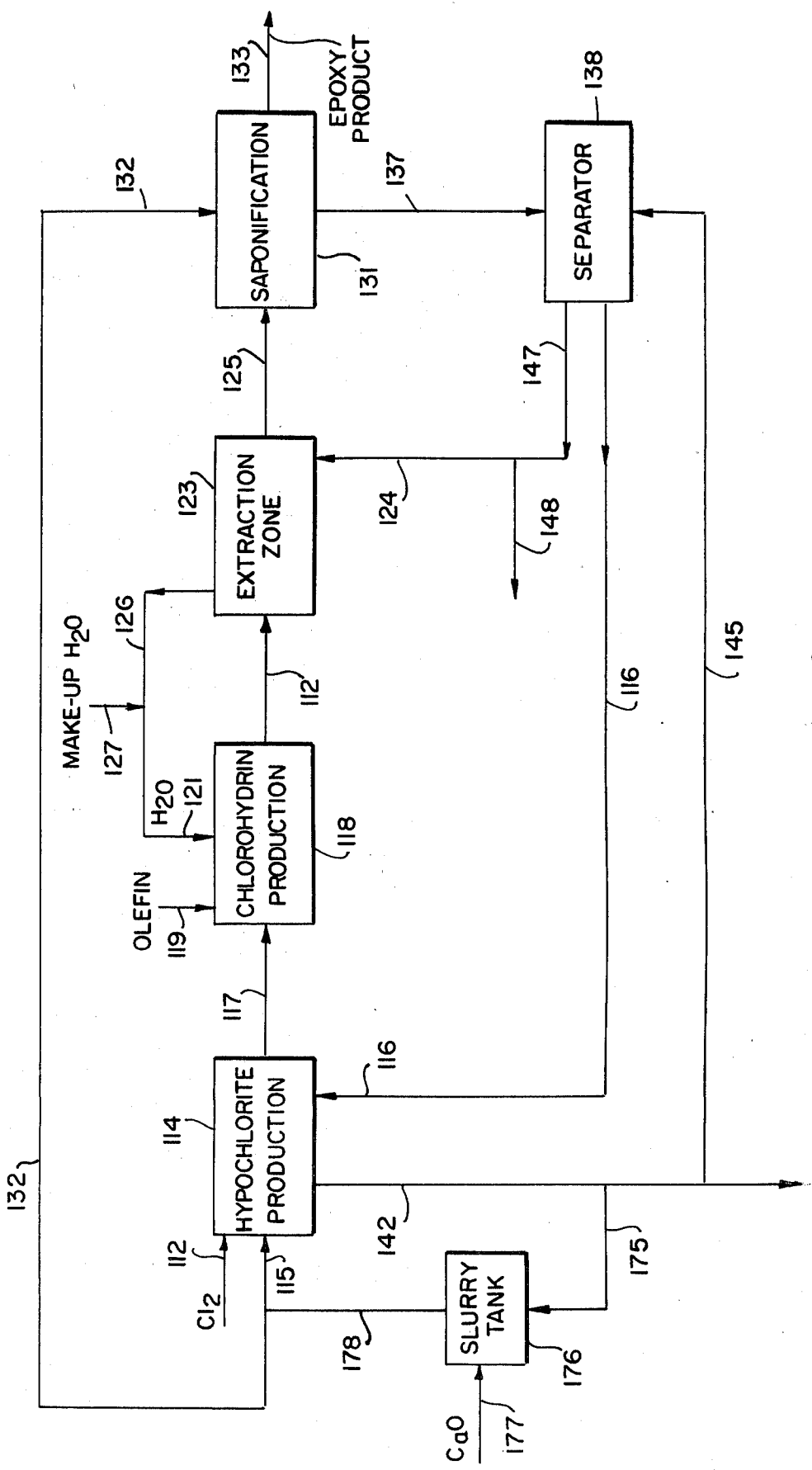

The invention will be further described with respect to preferred embodiments thereof, illustrated in the accompanying drawings wherein:

FIG. 1 is a simplified schematic flow diagram of an overall process in accordance with the invention; and FIG. 2 is a simplified schematic flow diagram of a preferred embodiment of the present invention.

The preferred embodiment will be particularly described with respect to the production of propylene oxide (1,2-epoxypropane), but it is to be understood that the embodiment is also applicable to production of other epoxy compounds; e.g., epichlorohydrin.

Referring now to FIG. 1 of the drawings, chlorine in line 10 and a slurry of calcium oxide in aqueous calcium chloride, having a calcium chloride concentration as hereinabove described, in line 11 are introduced into a hypochlorite production reaction zone, schematically generally indicated as 12. The hypochlorite production reaction zone 12 is also provided with tertiary alkanol through line 13, with such tertiary alkanol being provided by itself, or in an aqueous calcium chloride phase, which as hereinabove described, may also contain calcium oxide.

In the hypochlorite production reactor, the tertiary alkanol is chlorinated to tertiary alkyl hypochlorite, and in addition, an aqueous calcium chloride solution is produced.

Tertiary alkyl hypochlorite reaction product is withdrawn from reactor 12 through line 14, and an aqueous calcium chloride solution having a calcium chloride concentration as hereinabove described is withdrawn from reaction zone 12 through line 15.

A portion of the aqueous calcium chloride solution in line 15 is passed through line 16 and introduced into a slurry tank 17 wherein calcium oxide in line 18 and water, if required, in line 19 is added thereto to provide a slurry of calcium oxide in an aqueous calcium chloride solution for use in the hypochlorite production and saponification of chlorohydrin. The slurry is withdrawn from tank 17 through line 21 and a portion thereof introduced into the hypochlorite production reaction zone 12 through line 11, as hereinabove described.

Net aqueous calcium chloride is recovered from the hypochlorite production reaction zone 12 through line 22. Such aqueous calcium chloride may be purified to remove organics, and is then further treated to effect concentration and solidification thereof to thereby recover calcium chloride as net product.

The alkyl hypochlorite in line 14 is introduced into a chlorohydrin production zone, schematically generally indicated as 31 along with an olefin, such as propylene in line 32 and water in line 33. As hereinabove described, in zone 31, there is produced tertiary alkanol and chlorohydrin corresponding to the olefin feed.

As hereinabove described, the tertiary alkanol may be directly recovered from the chlorohydrin effluent for recycle to the hypochlorite production zone, with such recycle being effected through lines 34 and 13. In addition, an aqueous phase is internally recycled in the chlorohydrin production zone.

Similarly, as hereinabove described, an organic extraction solvent may be employed in zone 31 in order to extract organics from the effluent and provide as aqueous internal recycle stream. In accordance with such an embodiment, the organic extraction solvent includes the chlorohydrin as well as the tertiary alkanol.

Chlorohydrin produced in zone 31 is introduced into a saponification zone 41 through line 42. The feed in line 42 may be the chlorohydrin itself, or may be the chlorohydrin and tertiary alkanol in the organic extraction solvent. Calcium oxide slurried in aqueous calcium chloride is provided to the saponification zone 41 through line 43.

In the saponification zone 41, the chlorohydrin is saponified to the corresponding epoxy compound, and aqueous calcium chloride is generated as by-product. The epoxy compound is recovered as product through line 44.

In accordance with the embodiment wherein tertiary alkanol is present in the feed to the saponification zone 41, as hereinabove described, such tertiary alkanol is recovered in an aqueous calcium chloride phase for recycle to the hypochlorite production. Such tertiary alkanol recycle is effected through lines 45 and 13. In accordance with such an embodiment, the net calcium chloride produced in the saponification reaction zone 41 is recovered from the hypochlorite production zone 12 along with the calcium chloride produced in such hypochlorite production zone.

In accordance with the embodiments of the invention wherein tertiary alkanol is not introduced into the saponification zone 41, aqueous calcium chloride is recovered through line 46, and may be treated as product in a manner similar to the aqueous calcium chloride produced in the hypochlorite production zone. Similarly, in the case where the tertiary alkanol is present in the feed, and where such tertiary alkanol is initially recovered in the organic solvent, followed by extraction with calcium chloride from the hypochlorite production reactor, net aqueous calcium chloride is recovered from the saponification zone 41 through line 46.

Organic solvent, if present in the saponification reaction zone 41, is recovered therefrom and recycled to the chlorohyrin production (not shown).

The invention will be further described with respect to a particularly preferred embodiment as illustrated in FIG. 2.

Referring to FIG. 2 of the drawings, chlorine in line 112 is introduced into a hypochlorite production reactor, schematically indicated as 114 wherein the chlorine contacts a tertiary alkanol; in particular, tertiary butanol, dissolved in aqueous calcium chloride, introduced through line 116, and obtained as hereinafter described. In addition, a slurry of calcium oxide in aqueous calcium chloride is introduced into zone 114 through line 115.

The hypochlorite production reactor 114 is operated as hereinabove described to effect chlorination of the tertiary butanol to tertiary butyl hypochlorite, which is recovered as an organic stream through line 117.

The production of the hypochlorite and the recovery of the hypochlorite may be conducted as described in U.S. Pat. No. 4,008,133, which is hereby incorporated by reference.

The hypochlorite in line 117 is introduced into a chlorohydrin production reaction zone, schematically generally indicated as 118. Propylene, in line 119, as well as a recycled aqueous stream in line 121 are also introduced into the chlorohydrin production reaction zone 118. The chlorohydrin production reaction zone 118 is operated at conditions as hereinabove described to effect conversion of the propylene to propylene chlorohydrin. Such chlorohydrin production may be conducted as described in U.S. Pat. No. 4,008,133. It is also to be understood that in some cases a catalyst may be introduced into the chlorohydrin production zone in order to increase chlorohydrin production rate.

A liquid reaction effluent, which contains water, tertiary butanol, propylene chlorohydrin, as well as any reaction by-products, is withdrawn from the propylene chlorohydrin production reactor 118 through line 122, and introduced into an extraction zone, schematically generally indicated as 123, wherein the effluent is contacted with an organic extraction solvent introduced through line 124. In particular, the organic extraction solvent could be, for example, dichloropropane, carbon tetrachloride, or mixtures thereof. As a result of such contact, organics present in the chlorohydrin production reaction effluent are extracted into the organic solvent phase which is withdrawn from the extraction zone 123 through line 125.

An aqueous raffinate is withdrawn from extraction zone 123 through line 126, and in some cases, such aqueous raffinate may include some organic solvent, as well as residual tertiary butanol. If required, such organics may be removed in a separate operation. The aqueous rafinate in line 126, with or without treatment to remove organics, if required, is combined with make-up water in line 127 and introduced through line 121 into the propylene chlorohydrin production reactor 118.

The organic extract in line 125 is introduced into a saponification reaction zone, which is preferably in the form of a combination saponifier-stripping tower, which is schematically generally indicated as 131. In the saponification reaction zone 131, the organic extract is contacted with a slurry of calcium oxide in aqueous calcium chloride introduced through line 132. As a result of such contact, the propylene chlorohydrin is converted to propylene oxide and the hydrogen chloride released is neutralized by the calcium oxide to produce calcium chloride and water.

Crude propylene oxide, which may contain light end products, such as acetone, is withdrawn from the saponificationn reactor-stripping tower 131 through line 133 for purification thereof.

Referring back to the saponifier-stripping tower, schematially indicated as 131, a bottoms containing water, calcium chloride, tertiary butanol, organic solvent, as well as heavier by-products, is withdrawn from the stripping portion of the saponifier through line 137 and introduced into a separator, schematically generally indicated as 138 in order to effect separation of organic and aqueous phases. In accordance with one embodiment, separator 138 is further provided with aqueous calcium chloride, in line 145, derived from the hypochlorite production reactor 114, with such aqueous calcium chloride increasing the alkanol carrying capacity of the aqueous phase by increasing the bulk volume thereof. It is to be understood, however, that in some cases the separation can be conducted without the addition of further aqueous material.

It is also to be understood that the bulk carrying capacity of the aqueous phase could also be increased by the use of a portion of the slurry of calcium oxide in aqueous calcium chloride which is to be employed as feed to the hypochlorite production reactor 114.

The separation in separator 138 is effected in a manner such that the equilibrium concentration of tertiary butanol is in favor of the aqueous calcium chloride phase.

An aqueous calcium chloride phase, which contains tertiary butanol, is withdrawn from separator 138 through line 116 for introduction into the hypochlorite production reactor 114.

An aqueous calcium chloride solution having a concentration as hereinabove described, is withdrawn from the hypochlorite production reactor 114 through 142. A portion of such aqueous calcium chloride solution may be passed through line 145 as hereinabove described.

A further portion of such aqueous calcium chloride solution in line 175 is introduced into a slurry tank, schematically generally indicated as 176 wherein calcium oxide, in line 177 is slurried therein. Make-up water, as required, may also be provided to slurry tank 176. A slurry of calcium oxide in aqueous calcium chloride is withdrawn from slurry tank 176 through line 178 for use in both the saponification and hypochlorite production reactors.

Referring back to separator 138, an organic phase, containing the extraction solvent, as well as some tertiary butanol and heavier by-products, is withdrawn from separator 138 through line 147 for recycle to the extraction column 123 through line 124. A slip stream of such organic phase may be withdrawn through line 148 for purging of impurities.

As should be apparent, in accordance with the preferred embodiment, tertiary alkanol is effectively recovered for recycle to the hypochlorite production. In addition, by using a slurry of calcium oxide and calcium chloride, it is possible to obtain calcium chloride by-product in higher concentrations, thereby facilitating disposal and/or use of such calcium chloride.

It is to be understood that various modifications of such an embodiment are possible within the spirit and scope of the invention. Thus, for example, as hereinabove described, the tertiary alkanol present in the saponification effluent may be initially recovered in the organic phase, and subsequently extracted for use of aqueous calcium chloride from the hypochlorite production reactor. In such an embodiment, aqueous calcium chloride generated in the saponification is recovered without recycle to the hypochlorite production reactor.

The above modifications and others should be apparent to those skilled in the art from the teachings herein.

The present invention is particularly advantageous in that it provides an alternative means for producing an epoxy compound through the chlorohydrin without the use of sodium hydroxide, and which permits effective recovery of by-product without the problems heretofore encountered in the art in attempting to recover such by-products. Thus, in accordance with the present invention, by employing a slurry of calcium oxide in an aqueous solution of calcium chloride for both hypochlorite production and saponification, it is possible to recover calcium chloride as a concentrated solution thereof, and in some cases as a saturated solution.

Numerous modifications and variations of the present invention are possible in light of the above teachings, and, therefore, within the scope of the appended claims, the invention may be practised otherwise than as particularly described.

What is claimed:

1. In a process for producing an epoxy compound by chlorinating a tertiary alkanol to a tertiary alkyl hypochlorite, reacting the tertiary alkyl hypochlorite with water and olefinically unsaturated compound to produce the corresponding chlorohydrin and saponifying the chlorohydrin to the corresponding epoxy compound, the improvement comprising:

effecting chlorinating of the tertiary alkanol and said saponification with calcium oxide in an aqueous solution of calcium chloride having a combined concentration of calcium oxide and calcium chloride equivalent to at least 25 wt. percent expressed as calcium chloride; and recovering from said chlorinating and said saponification an aqueous solution of calcium chloride having a calcium chloride concentration of at least 25% by weight; combining calcium oxide with a portion of said recovered aqueous solution of calcium chloride to provide said calcium oxide in an aqueous solution of calcium chloride for the chlorinating and saponification.

2. The process of claim 1 wherein the combined concentration of calcium chloride and calcium oxide is at least 30%, by weight, expressed as calcium chloride.

3. The process of claim 1 wherein the combined concentration of calcium chloride and calcium oxide is from 30% to 45%, by weight, expressed as calcium chloride.

4. The process of claim 1 wherein the olefinically unsaturated compound is selected from the group consisting of propylene and allyl chloride.

5. The process of claim 4 wherein the tertiary alkanol is tertiary butanol.

6. The process of claim 1 wherein the tertiary alkanol has from 4 to 6 carbon atoms.

7. The process of claim 6 wherein the olefin is selected from the group consisting of alkenes having from 2 to 6 carbon atoms, styrene, cyclohexene, stilbene, butadiene, chloroprene, allyl chloride, allyl bromide, bromoprene and cyclopentene.

* * * * *